United States Patent [19]

Bell et al.

[11] 4,431,740

[45] Feb. 14, 1984

[54] DNA TRANSFER VECTOR AND TRANSFORMED MICROORGANISM CONTAINING HUMAN PROINSULIN AND PRE-PROINSULIN GENES

[75] Inventors: Graeme Bell; Raymond Pictet; Howard M. Goodman; William J. Rutter, all of San Francisco, Calif.

[73] Assignee: The Regents of the University of California, Berkeley, Calif.

[21] Appl. No.: 386,338

[22] Filed: Jun. 8, 1982

Related U.S. Application Data

[63] Continuation of Ser. No. 75,192, Sep. 12, 1979, abandoned.

[51] Int. Cl.$^3$ .................. C12N 1/20; C12N 15/00; C12N 1/00; C12P 21/00
[52] U.S. Cl. .................. 435/253; 435/68; 435/172; 435/317
[58] Field of Search ............... 435/172, 253, 317

[56] References Cited

U.S. PATENT DOCUMENTS 4,237,224 12/1980 Cohen et al. ................. 435/172

OTHER PUBLICATIONS

Crea et al., PNAS, USA, vol. 75, pp. 5765–5769, Dec. 1978.
Villa-Komaroff et al., PNAS, vol. 75, pp. 3727–3731, Aug. 1978.
Ullrich et al, Science, vol. 196, pp. 1313–1319, Jun. 17, 1977.
Ullrich et al., Proceedings of the Symposium on Proinsulin, Insulin and C-Peptide, pp. 20–26, Jul. 1978.
Chang et al., Nature, vol. 275, pp. 617–624, Oct. 1978.
Martial et al., Science, vol. 205, pp. 602–606, Aug. 1979.
Mercereau–Puijalon, Nature, vol. 275, pp. 505–510, Oct. 1978.
Goeddel et al., Proc. Nat. Acad. Sci., USA, vol. 76, pp. 106–110, Jan. 1979.
Goeddel et al., Nature, vol. 281, pp. 544–550, Oct. 1979.
O'Farrell et al., J. of Bacteriology, vol. 134, pp. 645–654, May 1978.
Englund, The Journal of Biological Chemistry, vol. 246, pp. 3269–3276 (1971).
Kemmler et al., The Journal of Biological Chemistry, vol. 246, pp. 6786–6791 (1971).
Englund, J. Mol. Biol., vol. 66, pp. 209–224 (1972).
Polisky et al., PNAS, USA, vol. 73, pp. 3900–3904 (1976).

*Primary Examiner*—Alvin E. Tanenholtz
*Attorney, Agent, or Firm*—Keil & Witherspoon

[57] ABSTRACT

A DNA having a base sequence coding for human proinsulin and a DNA having a base sequence coding for human pre-proinsulin have been cloned, and novel recombinant DNA transfer vectors containing said cloned DNAs have been constructed. Novel microorganisms transformed by said recombinant transfer vectors have been obtained. Certain of said transformed microorganisms have demonstrated capability to express the cloned DNA's, synthesizing a protein comprising human proinsulin and a protein-comprising human pre-proinsulin.

14 Claims, 2 Drawing Figures

FIG. 2

```
           -24              -20                                      -10
Human      met ala leu trp met arg leu leu pro leu leu ala leu leu ala leu trp gly
UCCUUCUGCCAUG GCC CUG UGG AUG CGC CUC CUG CCC CUG CUG GCG CUG CUG GCC CUC UGG GGA
                                                         ↑
                                                        Hha I 1                                  10
pro asp pro ala ala ala phe val asn gln his leu cys gly ser his leu val glu ala leu
CCU GAC CCA GCC GCA GCC UUU GUG AAC CAA CAC CUG UGC GGC UCA CAC CUG GUG GAA GCU CUC
                                                              ↑              ↑
                                                           Eco R II        Alu I
                                                              or
                                                           Bst N 1

20                                      30
tyr leu val cys gly glu arg gly phe phe tyr thr pro lys thr arg arg glu ala glu asp
UAC CUA GUG UGC GGG GAA CGA GGC UUC UUC UAC ACA CCC AAG ACC CGC CGG GAG GCA GAG GAC 40                                      50
leu gln val gly gln val glu leu gly gly gly pro gly ala gly ser leu gln pro leu ala
CUG CAG GUG GGG CAG GUG GAG CUG GGC GGG GGC CCU GGU GCA GGC AGC CUG CAG CCC UUG GCC
                            ↑
                          Alu I 60                                      70
leu glu gly ser leu gln lys arg gly ile val glu gln cys cys thr ser ile cys ser leu
CUG GAG GGG UCC CUG CAG AAG CGU GGC AUU GUG GAA CAA UGC UGU ACC AGC AUC UGC UCC CUC 80              86
tyr gln leu glu asn tyr cys asn
UAC CAG CUG GAG AAC UAC UGC AAC UAG ACGCAGCCCGCAGGCAGCCCCCCACCCGCCGCCUCCUGCACCGAGAG
         ⎛  ↑  ⎞
         ⎜Alu I⎟
         ⎝Pvu II⎠
```

AGAUGGAAUAAAGCCCUUGAACCAGC

DNA TRANSFER VECTOR AND TRANSFORMED MICROORGANISM CONTAINING HUMAN PROINSULIN AND PRE-PROINSULIN GENES

This is a continuation, of application Ser. No. 75,192, filed Sept. 12, 1979 and now abandoned.

BACKGROUND OF THE INVENTION

The invention herein provides the isolated and purified (hereinafter "cloned") human gene coding for proinsulin and the human gene coding for pre-proinsulin, methods for isolating and purifying the genes and a method for transferring the genes to and replicating the genes in a microorganism. The cloned genes are expressed by a host microorganism when fused with a host-expressable procaryotic gene. Both genes are useful in the production of human insulin for therapeutic purposes.

Insulin is a hormone produced primarily by the B cells of the pancreas. At the present time, the use of this hormone in the treatment of diabetis is well-known. Although slaughterhouses provide beef and pig pancreases as insulin sources, a shortage of this hormone is developing as the number of diabetics increases worldwide. Moreover, some diabetics develop an allergic reaction to beef and pig insulin, with deleterious effects. The ability to produce human insulin in quantities sufficient to satisfy world needs is therefore highly desirable. The present invention provides genes, which are insertable into microorganisms, which are useful in the production of human insulin.

Insulin consists of two polypeptide chains, known as the A and B chains, linked together by disulfide bridges. The A chain consists of 21 amino acids and the B chain consists of 30 amino acids. These chains are not synthesized independently in vivo but are derived from an immediate precursor, termed proinsulin: Proinsulin is a single polypeptide chain that contains a peptide, termed the C-peptide, which connects the A and B chains. See Steiner, D. F. et al., Science 157, 697 (1967). This C-peptide is excised during the packaging of insulin into the secretory granules of pancreatic B cells prior to secretion. See Tager, H. S. et al., Ann. Rev. Biochem. 43, 509 (1974). The current view of the function of the C-peptide is that it functions only in forming the three dimensional structure of the molecule. The amino acid sequence for human proinsulin, determined by conventional techniques, is given in Table 1. In this table the B chain is amino acids 1-30, the C-peptide is amino acids 31-65 and th A chain is amino acids 66-86.

TABLE 1

$$
\begin{aligned}
&\overset{1}{NH_2}-Phe-Val-Asn-Gln-His-Leu-Cys-Gly-Ser-\overset{10}{His}-\\
&Leu-Val-Glu-Ala-Leu-Tyr-Leu-Val-Cys-\overset{20}{Gly}-Glu-\\
&Arg-Gly-Phe-Phe-Try-Thr-Pro-Lys-\overset{30}{Thr}-Arg-Arg-\\
&Glu-Ala-Glu-Asp-Leu-Gln-Val-\overset{40}{Gly}-Gln-Val-Glu-\\
&leu-Gly-Gly-Gly-Pro-Gly-\overset{50}{Ala}-Gly-Ser-Leu-Gln-\\
&Pro-Leu-Ala-Leu-Glu-\overset{60}{Gly}-Ser-Leu-Gln-Lys-Arg-\\
&Gly-Ile-Val-Glu-\overset{70}{Gln}-Cys-Cys-Thr-Ser-Ile-Cys-\\
&Ser-Leu-Tyr-Gln-Leu-Glu-Asn-Try-Cys-\overset{86}{Asn}
\end{aligned}
$$

Chemical synthesis of this sequence of 86 amino acids though feasible is difficult conventional techniques.

In the pancreatic B cells, the initial translation product is not proinsulin itself, but a pre-proinsulin that contains more than 20 additional amino acids on the amino terminus of proinsulin. See Cahn, S. J. et al., Proc. Nat. Acad. Sci. U.S.A. 73, 1964 (1976) and Lomedico, P. T. et al., Nucl. Acid Res. 3, 381 (1976). The additional amino acid sequence is termed the signal peptide. In human pre-proinsulin (see FIG. 2), the signal peptide has twenty-four amino acids and the sequence is

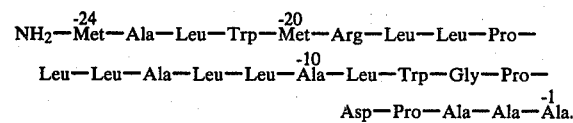

The twenty-four amino acid sequence is thought to be a specific signal for the vectorial transport of the synthesized polypeptide into the endoplasmic reticulum of the B cell, and is cleaved away from proinsulin during this phase. See Blobel, G. et al., J. Cell. Biol. 67, 835 (1975).

Several instances of signal peptides are known for eucaryotic proteins to be transported across membrane barriers. A specific cleavage enzyme has been observed in a cell-free system which hydrolyzes the peptide bond between the signal peptide and the active protein concomitant with passage through a cell membrane. (See, Blobel, G. et al., Proc. Nat. Acad. Sci U.S.A. 75, 361 (1978)).

Recent advances in biochemistry and in recombinant DNA technology have made it possible to achieve the synthesis of specific proteins under controlled conditions independent of the higher organism from which they are normally isolated. Such biochemical synthetic methods employ enzymes and subcellular components of the protein synthesizing machinery of living cells, either in vitro, in cell-free systems, or in vivo, in microorganisms. In either case, the key element is provision of a deoxyribonucleic acid (DNA) of specific sequence which contains the information necessary to specify the desired amino acid sequence. Such a specific DNA is herein termed a gene. The coding relationship whereby a deoxynucleotide sequence is used to specify the amino acid sequency of a protein is described briefly, infra, and operates according to a fundamental set of principles that obtain throughout the whole of the known realm of living organisms.

A cloned gene may be used to specify the amino acid sequence of proteins synthesized by in vitro systems. DNA-directed protein synthesizing systems are well-known in the art, see, e.g., Zubay, G., Ann. Rev. Genetics 7, 267 (1973). In addition, single-stranded DNA can be induced to act as messenger RNA in vitro, resulting in high fidelity translation of the DNA sequence (Salas, J. et al., J. Biol. Chem. 243, 1012 (1968). Other techniques well known in the art may be used in combination with the above procedures to enhance yields.

Developments in recombinant DNA technology have made it possible to isolate specific genes or portions thereof from higher organisms, such as man and other mammals, and to transfer the genes or fragments to a microorganisms, such as bacteria or yeast. The transferred gene is replicated and propagated as the transformed microorganism replicates. As a result, the transformed microorganism may become endowed with the capacity to make whatever protein the gene or fragment encodes, whether it be an enzyme, a hormone, an antigen or an antibody, or a portion thereof. The microorganism passes on this capability to its progeny, so that in effect, the transfer has resulted in a new strain, having the described capability. See, for example, Ullrich, A. et al., Science 196, 1313 (1977), and Seeburg, P. H., et l., Nature 270, 486 (1977). A basic fact underlying the application of this technology for practical purposes is that DNA of all living organisms, from microbes to man, is chemically similar, being composed of the same four nucleotides. The significant differences lie in the sequences of these nucleotides in the polymeric DNA molecule. The nucleotide sequences are used to specify the amino acid sequences of proteins that comprise the organism. Although most of the proteins of different organisms differ from each other, the coding relationship between nucleotide sequence and amino acid sequence is fundamentally the same for all organisms. For example, the same nucleotide sequence which codes for the amino acid sequence of HGH in human pituitary cells, will, when transferred to a microorganism, be recognized as coding for the same amino acid sequence.

Abbreviations used herein are given in Table 2.

TABLE 2

| | |
|---|---|
| DNA—deoxyribonucleic acid | A Adenine |
| RNA—ribonucleic acid | T—Thymine |
| cDNA—complementary DNA | G—Guanine |
| (enzymatically synthesized | C—Cytosine |
| from an mRNA sequence) | U—Uracil |
| mRNA—messenger RNA | ATP—adenosine triphosphate |
| dATP—deoxyadenosine triphosphate | TTP—Thymidine triphosphate |
| | EDTA—Ethylenediaminetetraacetic acid |
| dGTP—deoxyguanosine triphosphate | |
| dCTP—deoxycytidine triphosphate | |

The coding relationships between nucleotide sequence in DNA and amino acid sequence in protein are collectively known as the genetic code, shown in Table 3.

TABLE 3

| Genetic Code | | | |
|---|---|---|---|
| Phenylalanine(Phe) | TTK | Histidine(His) | CAK |
| Leucine(Leu) | XTY | Glutamine(Gln) | CAJ |
| Isoleucine(Ile) | ATM | Asparagine(Asn) | AAK |
| Methionine(Met) | ATG | Lysine(Lys) | AAJ |
| Valine(Val) | GTL | Aspartic acid(Asp) | GAK |
| Serine(Ser) | QRS | Glutamic acid(Glu) | GAJ |
| Proline(Pro) | CCL | Cysteine(Cys) | TGK |
| Threonine(Thr) | ACL | Tryptophan(Try) | TGG |
| Alanine(Ala) | GCL | Arginine(Arg) | WGZ |
| Tyrosine(Tyr) | TAK | Glycine(Gly) | GGL |
| Termination signal | TAJ | | |
| Termination signal | TGA | | |

Key: Each 3-letter deoxynucleotide triplet corresponds to a trinucleotide of mRNA, having a 5'-end on the left and 3'-end on the right. All DNA sequences given herein are those of the strand whose sequence corresponds to the mRNA sequence, with thymine substituted for uracil. The letters stand for the purine or pyrimidine bases forming this deoxynucleotide sequence.

A = adenine
G = guanine
C = cytosine
T = thymine
X = T or C if Y is A or G
Y = A, G, C or T if X is C
Y = A or G if X is T
W = C or A if Z is A or G
W = C if Z is C or T
Z = A, G, C or T if W is C
Z = A or G if W is A
QR = TC if S is A, G, C or T
QR = AG if S is T or C
S = A, G, C or T if QR is TC
S = T or C if QR is AG
J = A or G
K = T or C
L = A, T, C or G
M = A, C or T An important feature of the code, for present purposes, is the fact that each amino acid is specified by a trinucleotide sequence, also known as a nucleotide triplet. The phosphodiester bonds joining adjacent triplets are chemically indistinguishable from all other internucleotide bonds in DNA. Therefore the nucleotide sequence cannot be read to code for a unique amino acid sequence without additional information to determine the reading frame, which is the term used to denote the grouping of triplets used by the cell in decoding the genetic message.

Many recombinant DNA techniques employ two classes of compounds, transfer vectors and restriction enzymes, to be discussed in turn. A transfer vector is a DNA molecule which contains, inter alia, genetic information which insures its own replication when transferred to a host microorganism strain. Examples of transfer vectors commonly used in bacterial genetics are plasmids and the DNA of certain bacteriophages. Although plasmids have been used as the transfer vectors for the work described herein, it will be understood that other types of transfer vectors may be employed. Plasmid is the term applied to any autonomously replicating DNA unit which might be found in a microbial cell, other than the genome of the host cell itself. A plasmid is not genetically linked to the chromosome of the host cell. Plasmid DNA's exist as double-stranded ring structures generally on the order of a few million daltons molecular weight, although some are greater than $10^8$ daltons in molecular weight. They usually represent only a small percent of the total DNA of the cell. Transfer vector DNA is usually separable from host cell DNA by virtue of the great difference in size between them. Transfer vectors carry genetic information enabling them to replicate within the host cell, in most cases independently of the rate of host cell division. Some plasmids have the property that their replication rate can be controlled by the investigator by variations in the growth conditions. By appropriate techniques, the plasmid DNA ring may be opened, a fragment of heterologous DNA inserted, and the ring reclosed, forming an enlarged molecule comprising the inserted DNA segment. Bacteriophage DNA may carry a segment of heterologous DNA inserted in place of certain non-essential phage genes. Either way, the transfer vectors serves as a carrier or vector for an inserted fragment of heterologous DNA.

Transfer is accomplished by a process known as transformation. During transformation, bacterial cells mixed with plasmid DNA incorporate entire plasmide molecules into the cells. Although the mechanics of the process remain obscure, it is possible to maximize the proportion of bacterial cells capable of taking up plasmid DNA and hence of being transformed, by certain empirically determined treatments. Once a cell has incorporated a plasmid, the latter is replicated within the cell and the plasmid replicas are distributed to the daughter cells when the cell divides. Any genetic information contained in the nucleotide sequence of the plasmid DNA can, in principle, be expressed in the host cell. Typically, a transformed host cell is recognized by its acquisition of traits carried on the plasmid, such as resistance to certain antibiotics. Different plasmids are recognizable by the different capabilities or combination of capabilities which they confer upon the host cell containing them. Any given plasmid may be made in quantity by growing a pure culture of cells containing the plasmid and isolating the plasmid DNA therefrom.

Restriction endonucleases are hydrolytic enzymes capable of catalyzing site-specific cleavage of DNA molecules. The locus of restriction endonuclease action is determined by the existence of a specific nucleotide sequence. Such a sequence is termed the recognition site for the restriction endonuclease. Restriction endonucleases from a variety of sources have been isolated and characterized in terms of the nucleotide sequence of their recognition sites. Some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single stranded ends are self-complementary, hence cohesive, and may be used to rejoin the hydrolyzed DNA. Since any DNA susceptible of cleavage by such an enzyme must contain the same recognition site, the same cohesive ends will be produced, so that it is possible to join heterologous sequences of DNA which have been treated with a restriction endonuclease to other sequences similarly treated. See Roberts, R. J., Crit. Rev. Biochem. 4, 123 (1976). Restriction sites are relatively rare, however the general utility of restriction endonucleases has been greatly amplified by the chemical synthesis of double stranded oligonucleotides bearing the restriction site sequence. Therefore virtually any segment of DNA can be coupled to any other segment simply by attaching the appropriate restriction oligonucleotide to the ends of the molecule, and subjecting the product to the hydrolytic action of the appropriate restriction endonuclease, thereby producing the requisite cohesive ends. See Heyneker, H. L., et al., Nature 263, 748 (1976) and Scheller, R. H. et al., Science 196, 177 (1977). An important feature of the distribution of restriction endonuclease recognition sites is the fact that they are randomly distributed with respect to reading frame. Consequently, cleavage by restriction endonuclease may occur between adjacent codons or it may occur within a codon.

More general methods of DNA cleavage or for end sequence modification are available. A variety of non-specific endonucleases may be used to cleave DNA randomly, as discussed infra. End sequences may be modified by creation of oligonucleotide tails of dA on one end and dT at the other, or of dG and dC, to create sites for joining without the need for specific linker sequences.

The term "expression" is used in recognition of the fact than an oganism seldom if ever makes use of all its genetically endowed capabilities at any given time. Even in relatively simple organisms such as bacteria, many proteins which the cell is capable of synthesizing are not synthesized, although they may be synthesized under appropriate environmental conditions. When the protein product, coded by a given gene, is synthesized by the organism, the gene is said to be expressed. If the protein product is not made, the gene is not expressed. Normally, the expression of genes in E. coli is regulated as described generally, infra, in such manner that proteins whose function is not useful in a given environment are not synthesized and metabolic energy is conserved.

The means by which gene expression is controlled in E. coli is well understood, as the result of extensive studies over the past twenty years. See, generally, Hayes, W., The Genetics of Bacteria And Their Viruses, 2d edition, John Wiley & Sons, Inc., New York (1968), and Watson, J. D., The Molecular Biology of the Gene 3d edition, Benjamin, Menlo Park, Calif. (1976). These studies have revealed that several genes, usually those coding for proteins carrying out related functions in the cell, are found clustered together in continuous sequence. The cluster is called an operon. All genes in the operon are transcribed in the same direction, beginning with the codons coding for the N-terminal amino acid of the first protein in the sequence and continuing through to the C-terminal end of the last protein in the operon. At the beginning of the operon, proximal to the N-terminal amino acid codon, there exists a region of the DNA, termed the control region, which includes a variety of controlling elements including the operator, promoter and sequences for the ribosomal binding sites. The function of these sites is to permit the expression of those genes under their control to be responsive to the needs of the organism. For example, those genes coding for enzymes required exclusively for utilization of lactose are normally not appreciably expressed unless lactose or an analog thereof is actually present in the medium. The control region functions that must be present for expression to occur are the initiation of transcription and the initiation of translation. Expression of the first gene in the sequence is initiated by the initiation of transcription and translation at the position coding for the N-terminal amino acid of the first protein of the operon. The expression of each gene downstream from that point is also initiated in turn, at least until a termination signal or another operon is encountered with its own control region, keyed to respond to a different set of environmental cues. While there are many variations in detail on this general scheme, the important fact is that, to be expressed in a procaryote such as E. coli, a gene must be properly located with respect to a control region having initiator of transcription and initiator of translation functions.

It has been demonstrated that genes not normally part of a given operon can be inserted within the operon and controlled by it. The classic demonstration was made by Jacob F., et al., J. Mol. Biol. 13, 704 (1965). In that experiment, genes coding for enzymes involved in a purine biosynthesis pathway were transferred to a region controlled by the lactose operon. The expression of the purine biosynthetic enzyme was then observed to be repressed in the absence of lactose or a lactose analog, and was rendered unresponsive to the environmental cues normally regulating its expression.

In addition to the operator region regulating the initiation of transcription of genes downstream from it, there are known to exist codons which function as stop signals, indicating the C-terminal end of a given protein. See Table 3. Such codons are known as termination signals and also as nonsense codons, since they do not normally code for any amino acid. Deletion of a termination signal between structural genes of an operon creates a fused gene which could result in the synthesis of a chimeric protein consisting of two amino acid sequences coded by adjacent genes, joined by a peptide bond. That such chimeric proteins are synthesized when genes are fused was demonstrated by Benzer, S., and Champe, S. P., Proc. Nat. Acad. Sci U.S.A. 48, 114 (1962).

Once a given gene has been isolated, purified and inserted in a transfer vector, the over-all result of which is termed the cloning of the gene, its availability in substantial quantity is assured. The cloned gene is transferred to a suitable microorganism, wherein the gene replicates as the microorganism proliferates and from which the gene may be reisolated by conventional means. Thus is provided a continuously renewable source of the gene for further manipulations, modifications and transfers to other vectors or other loci within the same vector.

Expression is obtained by transferring the cloned gene, in proper orientation and reading frame, into a control region such that read-through from the procaryotic gene results in synthesis of a chimeric protein comprising the amino acid sequence coded by the cloned gene. A variety of specific protein cleavage techniques may be used to cleave the chimeric protein at a desired point so as to release the desired amino acid sequence, which may then be purified by conventional means. Techniques for constructing an expression transfer vector having the cloned gene in proper juxtaposition with a control region are described in Polisky, B., et al., Proc. Nat. Acad. Sci U.S.A. 73, 3900 (1976); Itakura, K., et al., Science 198, 1056 (1977); Villa-Komaroff, L., et al., Proc. Nat. Acad. Sci U.S.A. 75, 3727 (1978); Mercereau-Puijalon, O., et al., Nature 275, 505 (1978); Chang, A. C. Y., et al., Nature 275, 617 (1978), and in U.S. Application Ser. No. 933,035 by Rutter, et al., said application incorporated herein by reference as though set forth in full.

In summary, the process whereby a mammalian protein, such as human pre-proinsulin or proinsulin, is produced with the aid of recombinant DNA technology first requires the cloning of the mammalian gene. Once cloned, the gene may be produced in quantity, further modified by chemical or enzymic means and transferred to an expression plasmid. The cloned gene is also useful for isolating related genes, or, where a fragment is cloned, for isolating the entire gene, by using the cloned gene as a hybridization probe. Further, the cloned gene is useful in proving by hybridization, the identity or homology of independent isolates of the same or related genes. Because of the nature of the genetic code, the cloned gene, when translated in the proper reading frame, will direct the production only of the amino acid sequence for which it codes and no other.

Some work has been performed on the isolation and purification of rat proinsulin. Ullrich, A. et al., supra, and Villa-Komaroff, L. et al., supra describe the isolation and purification of the rat proinsulin gene and a method for transferring this gene to and replicating this gene in a microorganism. Ullrich et al. recovered several recombinant plasmids which contained the coding sequence for proinsulin, the 3' untranslated region and a part of the prepeptide. Expression of the rat DNA containing the insulin coding sequence was disclosed in application No. 933,035. Villa-Komaroff et al. recovered one recombinant plasmid which contained the coding sequence for amino acids 4-86 of proinsulin. This proinsulin sequence was separated from amino acids 24-182 of penicillinase, ($\beta$-lactamase) by the coding sequence for six glycines. This penicillinase-proinsulin coding sequence was expressed to produce a fused protein. These articles describe some of the basic procedures utilized in recombinant DNA technology. However, they do not describe the isolation and purification of the human pre-proinsulin gene or human proinsulin gene.

A different gene approach to obtain human insulin has been taken by Crea, R. et al., Proc. Nat. Acad. Sci U.S.A. b 75, 5765 (1978). This approach is to chemically synthesize coding sequences for (1) the A chain and (2) the B chain of human insulin, using codons favored by E. Coli. These two sequences can then be inserted into plasmids which can be expressed to produce the A and B chains. Human insulin could then be generated by formation of the correct disulfide bonds between the two protein chains.

The cloned gene for human pre-proinsulin is useful in a variety of ways. Transposition to an expression transfer vector will permit the synthesis of pre-proinsulin by a host microorganism transformed with the vector carrying the cloned gene. Growth of the transformed host will result in synthesis of pre-proinsulin as part of a chimeric protein. If the procaryotic portion of the fusion protein is the signal portion of an excreted or otherwise compartmentalized host protein, excretion or compartmentalization can occur greatly enhancing the stability and ease of purification of the pre-proinsulin fusion protein. Additionally, where the procaryotic portion is short, excretion from the procaryotic host may be facilitated by the prepeptide itself, if the presequence functions in the procaryotic host as it does in the eucaryotic cell. The pre-proinsulin gene may also be used to obtain the proinsulin gene using techniques as described below.

The cloned pre-proinsulin gene can be used in a variety of techniques for the production of pre-proinsulin. Pre-proinsulin itself is useful because it can be converted to proinsulin by known enzymatic and chemical techniques. For example, the prepeptide can be removed by a soluble enzymatic preparation, as described by Blobel, G. et al., supra, specific for removal of signal peptides. The cloned proinsulin gene can be used in a variety of techniques for the production of proinsulin. The proinsulin, produced from either gene, itself is useful because it can be converted to insulin by known enzymatic and chemical techniques. See Kemmber, W., et al., J. Biol. Chem. 242, 6786 (1971).

SUMMARY OF THE INVENTION

As disclosed herein, a cDNA having the base sequence coding for human pre-proinsulin and a cDNA having the base sequence coding for human proinsulin have been cloned. The structure of the cloned cDNAs have been verified by nucleotide sequence analysis.

The original source of genetic material was human insulinoma (an insulin producing tumor). Messenger RNA was isolated from the cells.

DNA complementary to the isolated messenger RNA (cDNA) was synthesized using reverse transcriptase, in two reaction cycles to generate double-stranded cDNA. The uncleaved, heterogeneous, double-stranded cDNA was treated to provide specific linker oligonucleotide sequences at each end, to facilitate insertion into a site of the same restriction specificity on a transfer vector.

For cloning, a transfer vector providing good selection and stable replication properties was selected. The treated cDNA was inserted into a transfer vector at a predetermined site on the vector DNA to form a recombinant transfer vector, using currently available techniques. Host microorganism cells were transformed with the recombinant vector. Transformants were selected according to the criteria established for insertion at the predetermined site. Single colonies, each derived from a single transformed microorganism cell, were picked and grown in individual cultures to permit replication of the recombinant transfer vector DNA clones. Transfer vector DNA was screened for insulin sequences by a modified colony hybridization method. Colonies yielding recombinant transfer vector DNA for insulin sequences were grown in larger individual cultures to isolate transfer vector DNA and to subject it to analysis. Appropriate clones were selected for definitive identification of the nucleotide sequence of the cloned pre-proinsulin or proinsulin genes, and for transfer to appropriate expression plasmids.

DETAILED DESCRIPTION OF THE INVENTION

Figure 1:
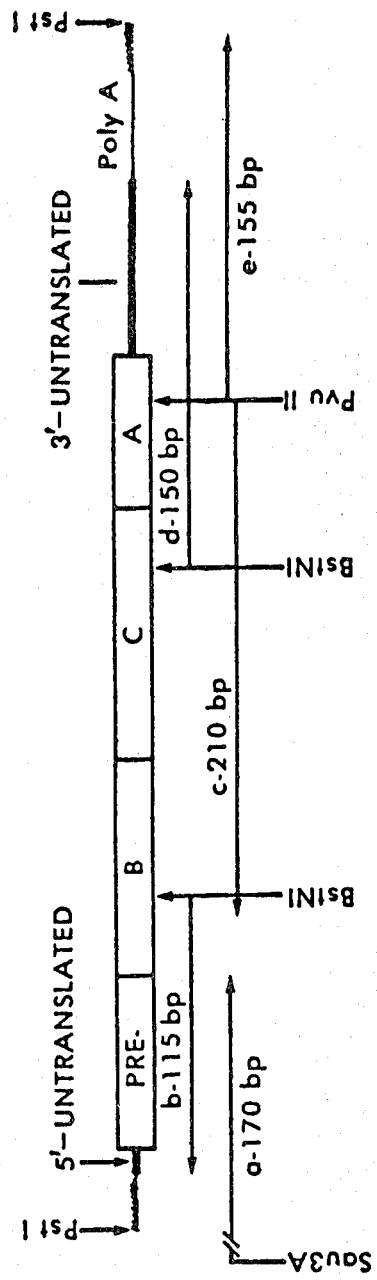

The present invention provides the essential genetic elements needed for the production of human insulin by techniques adapable to industrial processes. The naturally occurring structural gene has been cloned. Its expression in an appropriate host cell type, yields a protein product which is convertible to insulin by known methods. The present invention is fundamentally based upon the proinsulin molecule and takes advantage of the fact that the C-peptide region of the proinsulin molecule permits a spontaneous folding such that the A and B chains are properly juxtaposed. In such configuration, the correct pairing of sulfhydryl groups is assured and the formation of the disulfide cross links, as found in the active insulin molecule, are readily formed. Excision of the C-peptide is carried out by the combined use of trypsin, or an enzyme having similar substrate specificity, and carboxypeptidase B or cathepsin-B to remove a C-terminal arginine on the B strand, as described in the prior art.

The entire structural coding portion of the human insulin gene has been cloned as described herein, including a portion of the 5' untranslated region, all of the prepeptide sequence, the entire coding sequence for the B, C, and A peptides, and all of the 3' untranslated region. The choice of host cell will effect what portions of the cloned gene is used. The entire preproinsulin coding sequence will be useful in transforming certain species of higher eucaryotic cells, since the presequence acts as a signal peptide to promote excretion of the peptide from the cell. In addition, those eucaryotic cell lines capable of responding to the signal peptide will catalyze the specific removal of the presequence during transport of the protein across the cell membrane. In addition, such cells may be capable of further processing the expression product by excising the C-protein after catalyzing formation of the proper disulfide bonds.

In procaryotic host cells, use of the proinsulin coding sequence is presently preferred. The step of converting proinsulin to insulin is carried out in detail using techniques known in the art. Two types of expression are already known, both involve inserting the proinsulin coding sequence in a region of transfer vector DNA whose expression was controlled by a procaryotic promoter. In some cases, a portion of the procaryotic structural gene and the promoter control is interposed such that the expression product is a fusion protein having its N-terminal portion composed of the N-terminal part of the procaryotic protein and its C-terminal portion is the cloned sequence, in this instance, proinsulin. Expression of proinsulin as a fusion protein has the advantage that the fusion protein may be more stable in the host cell than proinsulin itself. In addition, where the procaryotic protein is one that is normally excreted from the host cell, the fusion protein may also be excreted, making it easier to purify the expression product. The use of fusion proteins has a disadvantage that they must be specifically cleaved to yield the desired product. In the case of proinsulin, techniques exist which take advantage of the sequence of the amino acid sequence of the protein, to specifically cleave a fusion protein, as described in Example 2.

The cloned coding sequence can also be expressed directly in the procaryotic cell by inserting the sequence directly adjacent to a promoter. The advantage in this instance is that specific cleavage is unnecessary. The principle disadvantage is that further purification is necessary.

The expression of mammalian genes inserted in $E.\ coli$ has now been obtained by insertion near the lac, trp and $\beta$-lactamase promoters. The lac promoter is useful because its genetics are well characterized. There are two possible insertion sites, providing long and short procaryotic leaders for the fusion protein. A large variety of genetic variants is available, having various levels of endogenous repressor, being temperature inducible and the like. The trp promoter has the advantage of providing high levels of expression when induced. Expression plasmids having insertion sites in the trp promoter are available for all three reading frames. The beta lactamase promoter provides what amounts to a procaryotic signal protein, since the lactamase is normally excreted. The $\beta$-lactamase fusion product is also excreted, or found in the periplasmic space. As a result, fewer purification steps will be required to achieve pure proinsulin.

The present invention takes advantage of the function of the C-peptide of proinsulin, namely to facilitate the spontaneous folding of proinsulin to bring the A and B chains together in the correct configuration such that the sulfhydryl groups are properly paired and the correct disulfide cross links are formed, as found in insulin isolated from nature. Comparison of the C-peptide sequences from various species shows that the C-peptide sequences are not highly conserved during evolution. Therefore, many substitutions of amino acids sequence are possible in the C-peptide. In fact, the function of the C-peptide may simply be a matter of providing an amino acid loop of proper length to allow the A and B chains to fall together in the proper configuration. Consequently, almost any coding sequence could be inserted in place of the C-peptide sequence of human proinsulin without substantially altering its primary function. There are, however, certain advantages favoring the use of the natural C-peptide; for example, removal of the peptide from the insulin preparations need not be complete, since the C-peptide is a natural component of insulin preparations. Furthermore, it may hold some advantage in conferring the proper configuration on the insulin or in removal by enzymes.

The present invention further demonstrates the universality of the genetic code. In particular, codons favored by mammalian cells are correctly translated in $E.\ coli$. Substitute codons, coding for the same amino acid, could be substituted in the sequence without affecting the sequence or function of the expressed protein.

Therefore, the present invention is intended to encompass all synthetic coding variants of the basic coding sequence actually cloned herein, insofar as such variants code for human preproinsulin and human proinsulin. The transformed microorganism, *Escherichia coli* X1776/pcHI-1, has been placed on deposition in the American Type Culture Collection, 12301 Parklawn Drive, Rockville, Md. 20852, ATCC accession number 31564. The plasmid pcHI-1 has also been placed on deposit, ATCC accesssion number 40022.

EXAMPLE 1

Cloned human pre-proinsulin gene. The human insulin gene was cloned from RNA isolated from human insulinoma using the procedure described by Ullrich, et al., supra for isolating RNA from islet cells. The RNA obtained as a pellet after centrifugation in 5.7 M CsCl containing 100 mM EDTA, was used without further fractionation as the template for cDNA synthesis using reverse transcriptase and S1 nuclease, as described by Ullrich, et al., supra. Approximately 40 ng of double stranded cDNA was prepared from 130 ug of unfractionated RNA.

The unfractionated cDNA was treated with terminal transferase in the presence of dCTP to generate oligo-C tails on the 3'-termini of the cDNA molecules. Similarly, the plasmid transfer vector pBR322 was cleaved with the restriction endonuclease Pst I and treated with terminal transferase in the presence of dGTP to generate oligo-dG tails on the 3'-termini of the linear plasmid DNA. The plasmid DNA thus treated cannot form a circular DNA since the single-stranded ends are not complementary. However, the oligo-dC ends of treated cDNA are complementary with the oligo-dC ends of the plasmid and can, therefore, be used to form circular plasmids having cDNA inserted at the Pst I site. Furthermore, the insertion regenerates both ends of the Pst I recognition sequences, at both ends of the insert, thereby providing for excision of the inserted sequences. (See Villa-Komeroff, et al, supra.)

The foregoing tailing procedure was used to generate pBR-322 plasmids having a hetrogeneous population of cDNA inserts at the Pst I site. Such plasmids would be ampicillinsensitive, since the Pst I site is in the β-lactamase gene, but remain tetracycline resistant. E. coli stain X1776 was transformed with the plasmid DNA containing inserts. Five hundred twenty-five tetracycline resistant transformants were obtained. These were replica-plated and screened for insulin sequences by in situ colony hybridization, essentially as described by Gruenstein and Hogness, Proc. Nat. Acad. Sci. USA 72, 3961 (1975). The previously cloned rat preproinsulin cDNA (Ullrich, A., et al, supra) was used as a hybridization probe, after labeling the rat cDNA by nick translation using DNA polymerase I. Since the amino acid sequences of rat and human insulins are quite similar (insulin, 92% homology; proinsulin, 83% homology), it was anticipated that the cloned rat cDNA would cross-hybridize with human insulin sequences under conditions of reduced stringency known in the art. Autoradiography revealed that two out of the 525 colonies hybridized with the cloned rat preproinsulin-I probe. Both colonies were ampicillinsensitive. The plasmids isolated from the colonies were approximately 250 base pairs (bp) and 500 bp longer than pBR322 itself. The larger plasmid was designated pcHI-1.

The nucleotide sequence of the inserted cDNA fragment of pcHI-1 was determined by the method of Maxam and Gilbert, Proc. Nat. Acad. Sci. USA 74, 560 (1977). A schematic diagram of the insert is shown in FIG. 1. The entire coding region for human pre-proinsulin was contained in the insert, together with a portion of the 5'-untranslated region, all of the 3'-untranslated region and part of the 3'-polydA region. The restriction sites used to cleave the insert for sequencing are also shown in FIG. 1, together with the direction of sequencing in each fragment and the regions of overlap.

The mRNA sequence derived from the cDNA sequence, and the amino acid sequence deduced from one of the reading frames is shown in FIG. 2. The primary structure of human proinsulin determined in this manner agrees precisely with that obtained by previous amino acid sequencing experiments (Dayhoff, M.D., Atlas of Protein Sequence and Stucture, 5, Supp. 2, pp. 127-130 (1976) and Suppl. 3, pp. 150-151 (1978). The amino acids of the proinsulin coding sequence are numbered from 1 to 86; those of the pre-sequence are numbered from −24 to −1. FIG. 2 further shows the location of certain restriction sites useful for the construction of the proinsulin gene from the pcHI-1 insert. It will be understood that the cDNA sequence of the coding strand of the pcHI-1 insert, is the same as that shown in FIG. 2 except that Thymine (T) is substituted for Uracil (U).

Large quantities of pcHI-1 and other plasmids are prepared by transforming *E. coli* HB-101 therewith. The HB-101 strain therefore serves as a convenient host for maintaining and replicating plasmids having cloned inserts as described herein.

EXAMPLE 2

Construction of proinsulin transfer vector. The insert cDMA of pcHI-1 contains the entire coding sequence for human pre-proinsulin. For certain applications, such as transfer to another species of eucaryotic cell, the normal processing and removal of the pre-sequence and C-peptide, and the attainment of a correctly folded configuration yielding active insulin may be expected. In other circumstances, transfer to a procaryotic cell such as a bacterium, may be expected to yield the unprocessed protein. In the latter situation, construction of a coding sequence for proinsulin will be advantageous, since proinsulin is readily converted to active insulin in vitro, using techniques well known in the art. See Kemmler, W., et al., J. Biol. Chem. 242, 6786 (1971). Three alternative methods for construction of a proinsulin coding sequence are disclosed herein. A plasmid transfer vector comprising pBR322 with an inserted proinsulin coding sequence is designated pcHP-1.

A. A chemically synthesized coding sequence for the human insulin B chain has been described by Crea, R., et al., Proc. Nat. Acad. Sci. USA, 75, 5765 (1978). The synthetic nucleotide sequence differs from the naturally occurring sequence disclosed herein because the synthetic sequence was designed to exploit codon assignments more favored by a procaryotic host, such as *E. coli*. Also, a triplet coding for methionine was incorporated just prior to amino acid 1 (phe). Fortuitously, however, the two sequences are identical in the region of amino acids 13-14, which region contains the only Alu I site common to both sequences. The locations of the Alu I sites on the natural sequence are shown in FIG. 2.

Synthetic proinsulin DNA is treated with Alu I endonuclease to yield two fragments of 43 bp and about 56 bp, respectively. Similarly, the cDNA insert of pcHI-1 preferably obtained by Hha I cleavage as described in Example 2B, is cleaved by partial hydrolysis catalyzed by Alu I endonuclease to form fragments of about 75, 90, 110, 135, 165, 200, 245 275, 375, and 455 bp, respectively; these are fractionated by gel electrophoresis to obtain the 375 by fragment, the result from a single site cleavage in the codon for amino acid number 14.

The synthetic gene cleavage fragments and the 375 bp single site cleavage fragment of the cDNA insert are joined by blunt-end ligation. Correct joining of the 43 bp synthetic fragment with the 375 bp cDNA fragment is maximized by providing that the 375 bp cDNA is present in molar excess. The possibilities for incorrect joining are also reduced by the fact that the synthetic fragments have single-stranded protruding ends that are not complementary with these of the 375 bp cDNA fragment.

The joined molecule, a composite of the synthetic sequence coding for methionine followed by amino acids 1–13, and the naturally occurring sequence coding for amino acids 14–86 of proinsulin, constitutes a coding sequence for proinsulin. The proinsulin coding sequence may be inserted in any chosen expression plasmid by either filling or excising the single-stranded ends and then attaching the appropriate linker oligonucleotides.

Expression yields a fusion protein which may be cleaved at the methionine residue by treatment with cyanogen bromide to yield proinsulin. Proinsulin is converted to insulin by the method of Kemmler, et al., supra.

B. The cDNA insert of pcHI-1 has a Hha I site in the sequence coding for amino acids -14 to -13, as shown in FIG. 2. In addition, the transfer vector pBR322 has a Hha I site just 22 bp from the Pst I site at the 5'-end of the insert. It is therefore possible to reisolate a sequence including all of the proinsulin coding sequence and a 22 bp region of pBR322 DNA, by treating pcHI-1 with Hha I endonuclease. This procedure is preferred to reisolating the insert with Pst I endonuclease, since the insert contains two internal Pst I sites and the yield of intact insert DNA by Pst I endonuclease treatment is low. The Hha I isolated sequence is also perfectly suitable for use in the procedures of Examples 2A and 2C herein.

Treatment of either isolate with Hha I endonuclease results in cleavage of the plus strand between amino acids $-14$ and $-13$ of the pre-sequence. (The plus strand is defined as the strand whose nucleotide sequence corresponds to the mRNA sequence. The minus strand is the strand whose sequence is complementary to the mRNA sequence.) The remaining presequence may be specifically removed by exploiting the 3' to 5' exonuclease activity of T4 DNA polymerase, which acts on the minus strand at the pre-sequence coding end, and on the plus strand at the opposite end. The exonucleolytic reaction may be stopped at a defined nucleotide by putting the same nucleotide, in triphosphate form, in the reaction mixture. The exonucleoytic action is then thwarted by the polymerase activity of the enzyme which continually replaces the specific nucleotide, as described by Englund, P. T. in J. Biol. Chem. 246, 3269 (1971) and in J. Mol. Biol. 66, 209 (1972).

The remaining pre-sequence may be digested specifically to the N-terminal phenylalanine codon of amino acid number 1 by three cycles of T4 polymerase digestion. Cycle 1 is carried out in the presence of TTP which will terminate digestion opposite the A of the glycine codon in amino acid position $-7$. Cycle 2 is carried out in the presence of dCTP, which terminates digestion opposite the G of codon position $-5$ (Asp). Cycle 3 is carried out in the presence of dATP which terminates digestion opposite the T which is the first nucleotide of position 1 of proinsulin.

After each cycle of T4 polymerase digestion, the triphosphate of the just-completed cycle must be removed and the triphosphate for the forthcoming cycle introduced. Minicolumns of Sephadex G-75[1/] are employed to separate triphosphates from the reaction mixture. The columns may be equilibrated with a suitable buffer and samples collected in a buffer containing the triphosphate of the succeeding cycle. In this way, enzyme comigrating with the DNA will not digest the DNA beyond the next selected stopping point. To prevent such digestion in the lower part of the column after resolution of the preceding triphosphate, the chromatography is carried out in the cold (4° C.) and elution is hastened by centrifugation. Alternatively, the enzyme is heat inactivated at 65° C. before the chromatography step. The succeeding cycle is then initiated by addition of fresh, active enzyme. As a result of three T4 polymerase digestion cycles, the minus strand of the DNA is digested completely and specifically to the first codon of the proinsulin coding sequence. The sequence of the plus strand at the opposite end of the molecule which also has a 3' end, is such that only a few nucleotides are removed by the foregoing cycles of digestion.

[1/] Trademark, Pharmacia, Inc., Uppsala, Sweden.

The plus strand at the pre-sequence end is then specifically digested with S1 exonuclease, which acts on single-stranded ends to yield a blunt-ended molecule. Care must be taken to prevent partial digestion by S1 nuclease beyond the beginning of the first codon. Such partial digestion may occur because of helix "breathing", a partial and transitory unpairing of DNA strands. Breathing occurs throughout the molecule but most frequently in A-T rich regions and at the ends of DNA molecules. A transitory unpairing at the A-T rich codon number 1 could permit S1 nucleolytic action beyond the desired stopping point. Such a result is prevented by carrying out S1 digestion under conditions of maximum helix integrity; low temperature (room temperature or less) and high salt which is normally employed in S1 reaction buffer.

Samples of DNA obtained at successive stages of S1 nuclease digestion are cloned into a suitable transfer vector according to procedures known in the art. Sequence analysis of the smallest Alu I fragment of such clones is used to screen for pro-insulin coding clones having the entire pre-sequence removed.

An attractive method for cloning the proinsulin-coding cDNA involves the incorporation of oligo-A tails, using terminal transferase, on the 3' ends of the cDNA. Oligo-T tails are generated on the 3'-end at a suitable site on an expression transfer vector, such as the EcoR1 site in the β-galactosidase gene on plasmid pTS-1 (Ullrich, A., et al) See also U.S. patent application No. 933,035, incorporated herein by reference). Insertion of the proinsulin-coding cDNA by the foregoing method yields a correctly oriented insert in phase as to reading frame with the β-galactosidase gene of the plasmid with a 1/6 probability. Expression of the oligo-A tails results in the incorporation of lysine residues just prior to the beginning of the proinsulin sequence. Mild trypsin digestion of the fusion protein yields proinsulin, which is converted to active insulin as previously described.

Alternatively, the fusion protein is treated with a combination of trypsin and carboxypeptidase B (or cathepsin B) to yield active insulin from the fusion protein in a single reaction.

C. A proinsulin coding sequence is constructed by selective cleavage at an internal site in the proinsulin coding region, followed by ligation of a chemically synthesized sequence coding for that part of the proinsulin coding region removed by the previous cleavage. The plasmid pcHI-1 is used as a source of the proinsulin coding region, which is selectively excised by treatment with Pst I endonuclease or preferably by treatment with Hha I endonuclease, as described in Example 2B.

Either fragment, after isolation is treated with alkaline phosphatase to remove the 5' terminal phosphate groups, then cleaved by treatment with a restriction endonuclease having a unique cleavage point in the proinsulin coding sequence. Preferably the restriction site is located near one of the ends of the proinsulin coding sequence. The Alu I site in region of amino acids 13–14 provides a convenient cleavage point (see FIG. 2). The Hha I fragment of pcHI-1 is partially cleaved with Alu I endonuclease to generate two fragments of approximately 76bp and approximately 375bp, respectively. The Alu I fragments are fractionated by gel electrophoresis, as described in Example 2A, and the 375bp fragment is recovered.

A nucleotide sequence coding for the first 13 amino acids of proinsulin with a 5'-terminal G (on the plus strand), to complete the codon for alanine at position 14, is synthesized by the phosphotriester method, Itakura, K., et al. J. Biol. Chem. 250, 4592 (1975) and Itakura, K., et al., J. AM. Chem. Soc. 97, 7327 (1975). The plus strand of the synthetic DNA has the sequence 5'-TTTGTGAACCAACACCTG TGCGGCTCACACCTGGTGGAAG-3', corresponding to the natural sequence. However, other sequences coding for the same amino acids may be synthesized. In general the sequence is 5'-TTKGTLAAK-CAJCAKXTYTGKGGLQRSCAKXTYGTLCAJG-3'. The resulting sequence is blunt-end ligated with the approximately 375bp fragment of the Hba I fragment of pcHI-1. Since the latter has a 5'-phosphate only at the end to be joined, the two fragments will be joined in the correct order. The synethetic fragment is correctly joined to the larger fragment in approximately 50% of the reactions.

The ligase-treated DNA is then cloned into a suitable expression plasmid, either by oligo-A tailing, as described in Example 2B, or by attachment or linkers and insertion into expression plasmids of known reading frames. In the case of oligo-A trailed inserts, expression of proinsulin is observed in about 1/12 of the clones. In the case of direct insertion where the reading frame is known to be correct, the frequency of expression clones is about 50%.

EXAMPLE 3

Expression of human preproinsulin and proinsulin. The cloned inserts coding for preproinsulin (Example 1) or proinsulin (Example 2) are inserted in an expression transfer vector. When the insertion occurs in the correct orientation with respect to initiation of translation at the insertion site, and the insert is in reading frame phase with the promotor and ribosome binding site, the protein product of the cloned gene is synthesized by actively metabolizing host cells transformed by the transfer vector. The protein product is a fusion protein if the expression transfer vector contains a portion of a procaryotic gene between the promoter and the insertion site. However the insertion may be made immediately adjacent to a promoter site. In such cases, the protein coded by the insert is synthesized directly. Both techniques present advantages and disadvantages. Fusion proteins have the advantage that they tend to stabilize the foreign protein coded by the inserted gene. Also, desirable functional properties such as excretion from the host cell are conferred by fusion with certain host proteins such as $\beta$-lactamase. On the other hand, purification of the insert coded sequence is complicated by the general desirability of specifically removing the host portion of the fusion protein. Such removal is accomplished by known techniques as described in Examples 2A and 2B. Direct synthesis of the desired protein obviates the need for specific cleavage but generally precludes the possibility of excretion from the host cell.

Expression plasmids have been developed wherein expression is controlled by the lac promoter (Itakura, et al., Science 198, 1056 (1977), Ullrich, A., et al., Excerpta Medica, (1979); by the trp promoter (Martial, et al., Science 205, 602 (1979); and by the $\beta$-lactamase promoter, U.S. application Ser. No. 44,647, incorporated herein by reference.

Expression is detected by measurement of a product capable of binding immunochemically with anti-insulin antibody, or anti-proinsulin antibody. Radioimmunoassay, in which the antibody is radioactively labeled and antigen-antibody pairs are precipitated by a preparation of heat-killed Staphyloccoccus aureus C is employed. (See Morgan and Lazarow, Diabetes 12, 115 (1963) and Kessler, S. W., J. Immunol., 115, 1617 (1975). Radioimmune screening, as described by Erlich, H. A., et al., Cell 10, 681 (1978) or by Broome, S. and Gilbert, W., Proc. Nat. Acad. Sci. USA, 75, 2746 (1978), is used for detecting expression in bacterial colonies.

Fusion proteins indicative of expression are detected by comparing molecular weights of the host protein contributing the N-terminal part of the fusion protein, in host cells transformed by expression plasmids with and without an insert. A preferred variant is to employ the minicell-producing E. coli strain P678-54 as host. Radioactively labeled amino acids are incorporated into minicell proteins, comparing strains transformed with expression transfer vectors with and without the inserted proinsulin coding sequence. The proteins are fractionated by SDS-acrylamide gel electrophoresis and the protein positions detected by autoradiography. Expression of proinsulin is indicated by the presence of a labeled protein band found only in minicells transformed by the proinsulin expression plasmid. The position of the electrophoretic band provides a measure of the molecular weight of the expressed protein, and is consistent with the known length of the inserted gene and of the N-terminal procaryotic portion.

Removal of the procaryotic portion and conversion of proinsulin to insulin in vitro are carried out by known procedures, as described in detail supra.

What is claimed is:

1. A DNA transfer vector comprising an inserted cDNA consisting essentially of a deoxynucleotide sequence coding for human pre-proinsulin, the plus strand of said cDNA having a defined 5' end, said 5' end being the first deoxynucleotide of the sequence coding for said pre-proinsulin.

2. A DNA transfer vector comprising an inserted cDNA consisting essentially of a deoxynucleotide sequence coding for human proinsulin, the plus strand of said cDNA having a defined 5' end, said 5' end being the first deoxynucleotide of the sequence coding for said proinsulin.

3. A microorganisms transformed by the transfer vector of claim 1 or 2.

4. A DNA transfer vector comprising a deoxynucleotide sequence coding for human pre-proinsulin consisting essentially of a plus strand having the sequence:

5'—$_{-24}$GCL$_{-23}$X$_{-22}$TY$_{-22}$TGG$_{-21}$ATG$_{-20}$W$_{-1}$-$_9$GZ$_{-19}$X$_{-18}$TY$_{-18}$X$_{-17}$TY$_{-17}$CCL$_{-16}$X$_{-15}$TY$_{-15}$X$_{-14}$TY$_{-14}$GCL$_{-13}$X$_{-12}$TY$_{-12}$X$_{-11}$TY$_{-11}$GCL$_{-10}$X$_{-9}$TY$_{-9}$TGG$_{-8}$GGL$_{-7}$CCL$_{-6}$GAK$_{-5}$CCL$_{-4}$GCL$_{-3}$GCL$_{-2}$GCL$_{-1}$TTK$_1$GTL$_2$-AAK$_3$CAJ$_4$CAK$_5$X$_6$TY$_6$TGK$_7$GGL$_8$QR$_9$S$_9$CAK$_{10}$X$_{11}$TY$_{11}$GTL$_{12}$GAJ$_{13}$GCL$_{14}$X$_{15}$TY$_{15}$TAK$_{16}$-X$_{17}$TY$_{17}$GTL$_{18}$TGK$_{19}$GCL$_{20}$GAJ$_{21}$W$_{22}$GZ$_{22}$GCL$_{23}$TTK$_{24}$TTK$_{25}$TAK$_{26}$ACL$_{27}$CCL$_{28}$AAJ$_{29}$ACL$_{30}$W$_{31}$GZ$_{31}$W$_{32}$GZ$_{32}$GAJ$_{33}$GCL$_{34}$GAJ$_{35}$GAK$_{36}$X$_{37}$TY$_{37}$CAJ$_{38}$GTL$_{39}$GGL$_{40}$CAJ$_{41}$GTL$_{42}$GAJ$_{43}$X$_{44}$TY$_{44}$GGL$_{45}$GGL$_{46}$GGL$_{47}$CCL$_{48}$GGL$_{49}$GCL$_{50}$GGL$_{51}$QR$_{52}$S$_{52}$X$_{53}$TY$_{53}$CAJ$_{54}$CCL$_{55}$X$_{56}$TY$_{56}$GCL$_{57}$X$_{58}$TY$_{58}$GAJ$_{59}$GGL$_{60}$QR$_{61}$S$_{61}$X$_{62}$TY$_{62}$CAJ$_{63}$AAJ$_{64}$W$_{65}$GZ$_{65}$GGL$_{66}$ATM$_{67}$GTL$_{68}$GAJ$_{69}$CAJ$_{70}$TGK$_{71}$TGK$_{72}$ACL$_{73}$QR$_{74}$S$_{74}$ATM$_{75}$TGK$_{76}$QR$_{77}$S$_{77}$X$_{78}$TY$_{78}$TAK$_{79}$CAJ$_{80}$X$_{81}$TY$_{81}$GAJ$_{82}$AAK$_{83}$TAK$_{84}$TGK$_{85}$AAK$_{86}$TAGACGCAGCCCGCAGGCAGCCCCCCACCCGCCGCCTCCTGCACCGAGAGAGATGGAATAAAGCCCTTGAACCAGC poly A-3' wherein A is deoxyadenyl,
G is deoxyguanyl,
C is deoxycytosyl,
T is thymidyl,
J is A or G;
K is T or C;
L is A, T, C, or G;
M is A, C or T;
$X_n$ is T or C if $Y_n$ is A or G; and C if $Y_n$ is C or T;
$Y_n$ is A, G, C or T if $X_n$ is C, and A or G if $X_n$ is T;
$W_n$ is C or A if $Z_n$ is G or A, and C if $Z_n$ is C or T;
$Z_n$ is A, G, C or T if $W_n$ is C, and A or G if $W_n$ is A;
$QR_n$ is TC if $S_n$ is A, G, C or T, and AG if $S_n$ is T or C;
$S_n$ is A, G, C or T if $QR_n$ is TC, and T or C if $QR_n$ is AG; and, subscript numerals, n, refer to the position in the amino acid sequence of human proinsulin, to which each triplet in the nucleotide sequence corresponds, according to the genetic code, the amino acid positions being numbered from the amino end.

5. A DNA transfer vector comprising a deoxynucleotide sequence coding for human proinsulin consisting essentially of a plus strand having the sequence:

5'-TTK$_1$GTL$_2$AAK$_3$CAJ$_4$CAK$_5$X$_6$TY$_6$TGK$_7$GGL$_8$QR$_9$S$_9$CAK$_{10}$X$_{11}$TY$_{11}$GTL$_{12}$GAJ$_{13}$GCL$_{14}$X$_{15}$TY$_{15}$TAK$_{16}$X$_{17}$TY$_{17}$GTL$_{18}$TGK$_{19}$GCL$_{20}$GAJ$_{21}$W$_{22}$GZ$_{22}$GCL$_{23}$TTK$_{24}$TTK$_{25}$TAK$_{26}$ACL$_{27}$CCL$_{28}$AAJ$_{29}$ACL$_{30}$W$_{31}$GZ$_{31}$W$_{32}$GZ$_{32}$GAJ$_{33}$GCL$_{34}$GAJ$_{35}$GAK$_{36}$X$_{37}$TY$_{37}$CAJ$_{38}$GTL$_{39}$GGL$_{40}$CAJ$_{41}$GTL$_{42}$GAJ$_{43}$X$_{44}$TY$_{44}$GGL$_{45}$GGL$_{46}$GGL$_{47}$CCL$_{48}$GGL$_{49}$GCL$_{50}$GGL$_{51}$QR$_{52}$S$_{52}$X$_{53}$TY$_{53}$CAJ$_{54}$CCL$_{55}$X$_{56}$TY$_{56}$GCL$_{57}$X$_{58}$TY$_{58}$GAJ$_{59}$GGL$_{60}$QR$_{61}$S$_{61}$X$_{62}$TY$_{62}$CAJ$_{63}$AAJ$_{64}$W$_{65}$GZ$_{65}$GGL$_{66}$ATM$_{67}$GTL$_{68}$GAJ$_{69}$CAJ$_{70}$TGK$_{71}$TGK$_{72}$ACL$_{73}$QR$_{74}$S$_{74}$ATM$_{75}$TGK$_{76}$QR$_{77}$S$_{77}$X$_{78}$TY$_{78}$TAK$_{79}$CAJ$_{80}$X$_{81}$TY$_{81}$GAJ$_{82}$AAK$_{83}$TAK$_{84}$TGK$_{85}$AAK$_{86}$TAG-3' wherein A is deoxyadenyl,
G is deoxyguanyl,
C is deoxycytosyl,
T is thymidyl,
J is A or G;
K is T or C;
L is A, T, C, or G;
M is A, C or T;
$X_n$ is T or C if $Y_n$ is A or G; and C if $Y_n$ is C or T;
$Y_n$ is A, G, C or T if $X_n$ is C, and A or G if $X_n$ is T;
$W_n$ is C or A if $Z_n$ is G or A, and C if $Z_n$ is C or T;
$Z_n$ is A, G, C or T if $W_n$ is C, and A or G if $W_n$ is A;
$QR_n$ is TC if $S_n$ is A, G, C or T, and AG if $S_n$ is T or C;
$S_n$ is A, G, C or T if $QR_n$ is TC, and T or C if $QR_n$ is AG; and, subscript numerals, n, refer to the position in the amino acid sequence of human proinsulin, to which each triplet in the nucleotide sequence corresponds, according to the genetic code, the amino acid positions being numbered from the amino end.

6. A microorganism transformed by the transfer vector of claim 4 or 5.

7. The plasmid pcHI-1.

8. The plasmid pcHP-1.

9. A microorganism transformed by the plasmid of claim 7 or 8.

10. A microorganism as in claim 9 wherein the organism is *Escherichia coli*.

11. The microorganism as in claim 10 wherein the organism is *Escherichia coli* HB-101.

12. The DNA transfer vector of claim 4 wherein:
J is A in amino acid positions 4, 13, 21, 69 and 70;
J is G in amino acid positions 29, 33, 34, 38, 41, 43, 54, 59, 63, 64, 80 and 82;
K is T in amino acid positions 1 and 72;
K is C in amino acid positions −5, 3, 5, 7, 10, 16, 19, 24, 25, 26, 36, 71, 76, 79, 83, 84, 85 and 86;
L is A in amino acid positions −7, −4, −2, 27, 34 and 50;
L is T in amino acid positions −6, 14, 48 and 49;
L is C in amino acid positions −23, −16, −10, −3, −1, 8, 23, 28, 30, 45, 47, 51, 55, 57, 66 and 73;
L is G in amino acid positions −13, 2, 12, 18, 20, 39, 40, 42, 46, 60 and 68;
M is C in amino acid position 75;
M is T in amino acid position 67;
X is T in amino acid position 56;
X is C in amino acid positions −22, −18, −17, −15, −14, −12, −11, −9, 6, 11, 15, 17, 37, 53, 58, 62, 78 and 81;
X is G in amino acid position 44;
Y is A in amino acid position 17;
Y is G in amino acid positions −22, −17, −15, −14, −12, −11, −9, 6, 11, 37, 44, 53, 56, 58, 62 and 81;
Y is C in amino acid positions −18, 15 and 78;
W is C in amino acid positions −19, 22, 31, 32 and 65;
Z is C in amino acid position −19;
Z is A in amino acid position 22;
Z is G in amino acid positions 31 and 32;
Z is T in amino acid position 65;
QR is TC in amino acid positions 9, 62 and 77;
QR is AG in amino acid positions 52 and 74;
S is A in amino acid position 9; and
S is C in amino acid positions 52, 61, 74 and 77.

13. The DNA transfer vector of claim 5 wherein:

J is A in amino acid positions 4, 13, 21, 69 and 70;
J is G in amino acid positions 29, 33, 35, 38, 41, 43, 54, 59, 63, 64, 80 and 82;
K is T in amino acid positions 1 and 72;
K is C in amino acid positions 3, 5, 7, 10, 16, 19, 24, 25, 26, 36, 71, 76, 79, 83, 84, 85 and 86;
L is A in amino acid positions 27, 34 and 50;
L is T in amino acid positions 14, 48 and 49;
L is C in amino acid positions 8, 23, 28, 30, 45, 47, 51, 55, 57, 66 and 73;
L is G in amino acid positions 2, 12, 18, 20, 39, 40, 42, 46, 60 and 68;
M is C in amino acid position 75;
M is T in amino acid position 67;
X is T in amino acid position 56;
X is C in amino acid positions 6, 11, 15, 17, 37, 53, 58, 62, 78 and 81;
X is G in amino acid position 44;
Y is A in amino acid position 17;
Y is G in amino acid positions 6, 11, 37, 44, 53, 56, 58, 62 and 81;
Y is C in amino acid positions 15 and 78;
W is C in amino acid positions 22, 31, 32 and 65;
Z is A in amino acid position 22;
Z is G in amino acid positions 31 and 32;
Z is T in amino acid position 65;
QR is TC in amino acid positions 9, 62 and 77;
QR is AG in amino acid positions 52 and 74;
S is A in amino acid position 9; and
S is C in amino acid positions 52, 61, 74 and 77.

14. The DNA transfer vector of claim 5 wherein the codon for amino acid position one is preceded by 5'-ATG and
J is A in amino acid positions 13, 21, 69 and 70;
J is G in amino acid positions 4, 29, 33, 35, 38, 41, 43, 54, 59, 63, 64, 80 and 82;
K is T in amino acid positions 3, 7 and 72;
K is C in amino acid positions 1, 5, 10, 16, 19, 24, 25, 26, 36, 71, 76, 79, 83, 84, 85 and 86;
L is A in amino acid positions 27, 34, 50;
L is T in amino acid positions 8, 12, 14, 48 and 49;
L is C in amino acid positions 2, 23, 28; 30, 45, 47, 51, 55, 57, 66 and 73;
L is G in amino acid positions 18, 20, 39, 40, 42, 46, 60 and 68;
M is C in amino acid position 75;
M is T in amino acid position 67;
X is T in amino acid position 56;
X is C in amino acid positions 6, 11, 15, 17, 37, 53, 58, 62, 78, and 81;
X is G in amino acid position 44;
Y is A in amino acid position 17;
Y is G in amino acid positions 37, 44, 53, 56, 58, 62, and 81;
Y is C in amino acid positions 11, 15 and 78;
Y is T in amino acid position 6;
W is C in amino acid positions 22, 31, 32 and 65;
Z is A in amino acid position 22;
Z is G in amino acid positions 31 and 32;
Z is T in amino acid position 65;
QR is TC in amino acid positions 9, 62 and 77;
QR is AG in amino acid positions 52 and 74
S is T in amino acid position 9; and
S is C in amino acid positions 52, 61, 74 and 77.

* * * * *

UNITED STATES PATENT AND TRADEMARK OFFICE
CERTIFICATE OF CORRECTION

PATENT NO. : 4,431,740

DATED : FEBRUARY 14, 1984

INVENTOR(S) : GRAEME BELL ET AL

It is certified that error appears in the above-identified patent and that said Letters Patent is hereby corrected as shown below:

Column 1, line 22 "diabetis" should read --diabetes--; line 68, "difficult conventional" should read --difficult using conventional--.

Column 2, line 45 "sequency" should read --sequence--.

Column 3, insert between line 65 and 66 --X = C if Y is C or T--.

Column 4, line 61 "plasmide" should read --plasmid--.

Column 11, line 34 "oligo-dC" should read --oligo-dG--; line 44 and line 63 "ampicillinsensitive" should read --ampicillin sensitive--.

Column 12, line 35 "cDMA" should read --cDNA--.

Column 13, line 16 "these" should read --those--.

Col 1 Table 1, each occurrence "Try" should read --Tyr--.
Col 3 Table 2, "A Adenine" should read --A-Adenine--.
Col 3 Table 3, "Tryptophan(Try)" should read --Tryptophan(Trp)--.

UNITED STATES PATENT AND TRADEMARK OFFICE
CERTIFICATE OF CORRECTION

PATENT NO. : 4,431,740
DATED : FEBRUARY 14, 1984
INVENTOR(S) : GRAEME BELL ET AL

It is certified that error appears in the above-indentified patent and that said Letters Patent is hereby corrected as shown below:

Column 17:

Claim 4, line 11 of $GCL_{20}$" should read --$GGL_{20}$--;

Claim 4, line 12, "$CL_{23}$" should read --$GL_{23}$--;

Claim 5, line 6, "$GCL_{20}$" should read $GGL_{20}$--;

Claim 5, line 7, "$GCL_{23}$" should read --$GGL_{23}$--;

Column 15, Claim 12, line 3, "34" should read --35--.
Claim 12, line 31 "QR is TC in amino acid positions 9, 62 and 77; should read --QR is TC in amino acid positions 9, 61 and 77;--

Column 19, Claim 13, line 28 "QR" is TC in amino acid positions 9, 61 and 77;--

Column 20, Claim 14, line 31 "QR is TC in amino acid positions 9, 62 and 77;" should read --QR is TC is amino acid positions 9, 61 and 77;--.

Signed and Sealed this

Twenty-fifth Day of January, 1994

Attest:

BRUCE LEHMAN

*Attesting Officer*  *Commissioner of Patents and Trademarks*